(12) United States Patent
D'Arrigo et al.

(10) Patent No.: US 7,922,958 B2
(45) Date of Patent: Apr. 12, 2011

(54) METHOD OF MAKING AN ELONGATE SYRINGE BARREL

(75) Inventors: Christina Joy D'Arrigo, Hoboken, NJ (US); Eric Schiller, Kinnelon, NJ (US); Anthony Economou, Sparta, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 12/827,293

(22) Filed: Jun. 30, 2010

(65) Prior Publication Data

US 2010/0314796 A1 Dec. 16, 2010

Related U.S. Application Data

(62) Division of application No. 11/462,154, filed on Aug. 3, 2006.

(51) Int. Cl.
*B29C 45/36* (2006.01)
*B29C 45/44* (2006.01)

(52) U.S. Cl. ............... 264/318; 264/328.1; 249/59

(58) Field of Classification Search ............ 264/318, 264/328.1; 425/DIG. 58; 249/59
See application file for complete search history.

(56) References Cited

U.S. PATENT DOCUMENTS

| | | |
|---|---|---|
| 2,034,294 A | 3/1936 | Hein |
| 2,133,019 A * | 10/1938 | Campbell ............ 249/59 |
| 2,522,052 A | 9/1950 | Logan et al. |
| 2,711,171 A | 6/1955 | Dunnican |
| 2,834,346 A | 5/1958 | Adams |
| 2,855,297 A | 10/1958 | Saunders |
| 2,902,995 A | 9/1959 | Loper |
| 3,087,486 A | 4/1963 | Kilpatrick |
| 3,098,813 A | 7/1963 | Beebe et al. |
| 3,249,103 A | 5/1966 | Woodhouse |
| 3,352,306 A | 11/1967 | Hirsch |
| 3,402,713 A | 9/1968 | Senkowski et al. |
| 3,491,757 A | 1/1970 | Arce |

(Continued)

FOREIGN PATENT DOCUMENTS

CH 303837 2/1955

(Continued)

OTHER PUBLICATIONS

Electronic translation of JP 2003-275305.*

(Continued)

*Primary Examiner* — Jill L Heitbrink
(74) *Attorney, Agent, or Firm* — Jeanne P. Lukasavage

(57) ABSTRACT

A syringe and detachable needle assembly having binary attachment features include an elongate syringe barrel having a longitudinal axis, an open proximal end and an open distal end including a collar. The collar includes the cylindrically shaped sidewall having an inside surface and an outside surface. A needle assembly includes the hub having a body portion including a proximal end, a distal end and a conduit therethrough. A cannula having a distal end, a proximal end and a lumen therethrough is attached to the distal end of the hub so that the lumen is in fluid communication with the chamber. A lug is provided on one of the collar and the hub and a ramp and a rest surface is provided on the other of the collar and the hub. The ramp is oriented at an acute angle with respect to longitudinal axis for guiding the lug during needle assembly attachment, to the rest surface forcing the hub to contact the barrel to form a seal the hub and the barrel.

4 Claims, 17 Drawing Sheets

U.S. PATENT DOCUMENTS

| | | | |
|---|---|---|---|
| 3,682,162 A | | 8/1972 | Colyer |
| 3,828,780 A | | 8/1974 | Morrison, Jr. |
| 3,904,165 A | * | 9/1975 | Den Boer ............................ 249/67 |
| 3,943,932 A | | 3/1976 | Woo |
| 4,128,173 A | | 12/1978 | Lazarus et al. |
| 4,240,428 A | | 12/1980 | Akhavi |
| 4,301,802 A | | 11/1981 | Poler |
| 4,411,266 A | | 10/1983 | Cosman |
| 4,554,962 A | * | 11/1985 | Wright ............................ 249/59 |
| 4,644,960 A | | 2/1987 | Johans |
| 4,755,170 A | | 7/1988 | Bolden |
| 4,810,248 A | | 3/1989 | Masters et al. |
| 4,816,024 A | | 3/1989 | Sitar et al. |
| 4,824,433 A | | 4/1989 | Marz et al. |
| 4,832,696 A | | 5/1989 | Luther et al. |
| 4,834,718 A | | 5/1989 | McDonald |
| 4,846,811 A | | 7/1989 | Vanderhoof |
| 4,917,669 A | | 4/1990 | Bonaldo |
| 4,919,608 A | | 4/1990 | Catalanotti et al. |
| 4,929,241 A | | 5/1990 | Kulli |
| 4,944,725 A | | 7/1990 | McDonald |
| 4,964,854 A | | 10/1990 | Luther |
| 4,978,344 A | | 12/1990 | Dombrowski et al. |
| 4,994,041 A | | 2/1991 | Dombrowski et al. |
| 5,007,902 A | | 4/1991 | Witt |
| 5,049,136 A | | 9/1991 | Johnson |
| 5,051,109 A | | 9/1991 | Simon |
| 5,053,017 A | | 10/1991 | Chamuel |
| 5,085,648 A | | 2/1992 | Purdy et al. |
| 5,135,504 A | | 8/1992 | McLees |
| 5,147,327 A | | 9/1992 | Johnson |
| 5,186,712 A | | 2/1993 | Kelso et al. |
| 5,205,823 A | | 4/1993 | Zdeb |
| 5,215,525 A | | 6/1993 | Sturman |
| 5,215,528 A | | 6/1993 | Purdy et al. |
| RE34,416 E | | 10/1993 | Lemieux |
| 5,273,543 A | | 12/1993 | Bell et al. |
| 5,279,591 A | | 1/1994 | Simon |
| 5,281,385 A | | 1/1994 | Julian |
| 5,300,045 A | | 4/1994 | Plassche, Jr. |
| 5,312,359 A | | 5/1994 | Wallace |
| 5,322,517 A | | 6/1994 | Sircom et al. |
| 5,328,482 A | | 7/1994 | Sircom et al. |
| 5,395,347 A | | 3/1995 | Blecher et al. |
| 5,405,330 A | | 4/1995 | Zunitch et al. |
| 5,409,461 A | | 4/1995 | Steinman |
| 5,433,739 A | | 7/1995 | Sluijter et al. |
| 5,458,658 A | | 10/1995 | Sircom |
| 5,533,970 A | | 7/1996 | Berger et al. |
| 5,558,651 A | | 9/1996 | Crawford et al. |
| 5,562,633 A | | 10/1996 | Wozencroft |
| 5,573,510 A | | 11/1996 | Isaacson |
| 5,584,809 A | | 12/1996 | Gaba |
| 5,584,818 A | | 12/1996 | Morrison |
| 5,599,310 A | | 2/1997 | Bogert |
| 5,601,536 A | | 2/1997 | Crawford et al. |
| 5,605,539 A | | 2/1997 | Buelna et al. |
| 5,611,781 A | | 3/1997 | Sircom et al. |
| 5,613,952 A | | 3/1997 | Pressly, Sr. et al. |
| 5,624,694 A | * | 4/1997 | Delaby et al. ............................ 425/577 |
| 5,662,610 A | | 9/1997 | Sircom |
| 5,676,658 A | | 10/1997 | Erskine |
| 5,683,365 A | | 11/1997 | Brown et al. |
| 5,695,474 A | | 12/1997 | Daugherty |
| 5,697,907 A | | 12/1997 | Caba |
| 5,704,919 A | | 1/1998 | Kraus et al. |
| 5,713,876 A | | 2/1998 | Bogert et al. |
| 5,782,803 A | | 7/1998 | Jentzen |
| 5,807,395 A | | 9/1998 | Mulier et al. |
| 5,833,670 A | | 11/1998 | Dillon et al. |
| 5,833,674 A | | 11/1998 | Turnbull et al. |
| 5,855,568 A | | 1/1999 | Battiato et al. |
| 5,865,806 A | | 2/1999 | Howell |
| 5,879,337 A | | 3/1999 | Kuracina et al. |
| 5,882,337 A | | 3/1999 | Bogert et al. |
| 5,902,271 A | | 5/1999 | Jentzen |
| 5,911,705 A | | 6/1999 | Howell |
| 5,935,109 A | | 8/1999 | Donnan |
| 5,938,055 A | * | 8/1999 | Philips et al. ............................ 215/222 |
| 5,951,515 A | | 9/1999 | Osterlind |
| 5,976,110 A | | 11/1999 | Greengrass et al. |
| 6,001,080 A | | 12/1999 | Kuracina et al. |
| 6,004,294 A | | 12/1999 | Brimhall et al. |
| 6,012,213 A | | 1/2000 | Chang et al. |
| 6,117,108 A | | 9/2000 | Woehr et al. |
| 6,146,380 A | | 11/2000 | Racz et al. |
| 6,171,285 B1 | | 1/2001 | Johnson |
| 6,190,370 B1 | | 2/2001 | Tsui |
| 6,213,666 B1 | * | 4/2001 | Lang et al. ............................ 264/328.1 |
| 6,298,256 B1 | | 10/2001 | Meyer |
| 6,352,521 B1 | | 3/2002 | Prosl |
| 6,368,303 B1 | | 4/2002 | Caizza |
| 6,456,874 B1 | | 9/2002 | Hafer et al. |
| 6,485,475 B1 | | 11/2002 | Chelly |
| 6,629,957 B1 | | 10/2003 | Wiklund |
| 6,706,015 B2 | | 3/2004 | Bang |
| 6,840,291 B2 | | 1/2005 | Caizza et al. |
| 2001/0056275 A1 | | 12/2001 | Brushey |
| 2002/0173753 A1 | | 11/2002 | Caizza |
| 2004/0006312 A1 | | 1/2004 | Donnan et al. |
| 2004/0054336 A1 | | 3/2004 | Klint et al. |
| 2004/0122378 A1 | | 6/2004 | Hsu |

FOREIGN PATENT DOCUMENTS

| | | | |
|---|---|---|---|
| DE | 3721167 | | 1/1989 |
| EP | 0102538 | | 8/1983 |
| EP | 0747083 | | 12/1996 |
| EP | 0747085 | | 12/1996 |
| EP | 0750916 | | 1/1997 |
| EP | 0704225 | | 12/1999 |
| EP | 1205156 | | 5/2002 |
| GB | 2088215 | | 6/1982 |
| GB | 2343118 | | 5/2000 |
| JP | 2003-235992 | | 8/2003 |
| JP | 2003-275305 | * | 9/2003 |
| RU | 1391626 | | 4/1998 |
| WO | WO-94/23784 | | 10/1994 |
| WO | WO-98/19725 | | 5/1998 |
| WO | WO-98/57689 | | 12/1998 |
| WO | WO-99/08742 | | 2/1999 |
| WO | WO-00/06226 | | 2/2000 |
| WO | WO-02/45786 | | 6/2002 |
| WO | WO-2004/004812 | | 1/2004 |
| WO | WO-2004/032995 | | 4/2004 |
| WO | WO-2004/105842 | | 12/2004 |

OTHER PUBLICATIONS

Non-Final Office Action in U.S. Appl. No. 11/462,154, mailed March 31, 2010, 13 pgs.
Final Office Action in U.S. Appl. No. 11/462,154, mailed Jun. 30, 2009, 28 pgs.
International Search Report in PCT/US2007/017274, mailed Jan. 1, 2008, 3 pgs.
IPRP and Written Opinion in PCT/US2007/017274, dated Feb. 3, 2009, 7 pgs.
Non-Final Office Action in U.S. Appl. No. 11/462,154, mailed Nov. 19, 2008, 31 pgs.
New Paediatric Regional Anesthesia Product Range—B. Braun Melsungen AG, 2 pgs.
Non-Final Office Action in U.S. Appl. No. 11/697,903, mailed Jun. 15, 2009, 10 pgs.
PNA Medical Systems—Continuous Plexus Sets, www.pnamed.com/continuous.html Nov. 14, 2002, 5 pgs.
Product Profiles Plexus Anesthesia, www.bbraunusa.com/stimpulex/contiplex.html Nov. 14, 2002, 3 pgs.

* cited by examiner

METHOD OF MAKING AN ELONGATE SYRINGE BARREL

CROSS REFERENCE TO RELATED APPLICATIONS

This is a divisional application of application Ser. No. 11/462,154, filed Aug. 3, 2006, which is incorporated herein by reference.

FIELD OF THE INVENTION

The present invention relates to syringes with removable needle assemblies. More particularly, the present invention relates to syringes having binary attachment features, and a method of making a syringe barrel for the present invention.

BACKGROUND

Syringe assemblies designed for use with replaceable needle assemblies usually contain a luer slip or locking luer type fitting for securing the needle assembly to the syringe barrel. These connections rely on an elongate frusto-conically shaped syringe barrel tip which frictionally engages a frusto-conically shaped passageway in a needle hub. The relatively acute angle of the syringe tip, measured from the longitudinal axis of the syringe barrel, provides an excellent seal between the syringe tip and the hub. However, slight variations in the angle or diameter of the tapered surfaces of the syringe barrel and/or the needle hub produce large variations in the relative position of the needle hub with respect to the end of the barrel and, therefore, variations in dead space. The space inside the barrel tip and between the end of the barrel tip and the end of the cavity in the hub constitutes a dead space containing liquid that cannot be delivered by the syringe.

In the case of expensive medications and multi-patient immunization programs, medication lost in the dead space can become costly. This is especially true in immunization programs involving thousands of people. Controlling dead space to a minimum may result in more people being immunized with the same amount of medication provided for the program.

The prior art also teaches a flat seal, perpendicular to the longitudinal axis of the syringe barrel which mates with a complimentary flat seal on the needle hub for use with a threaded needle assembly and barrel engagement structure. The flat seal reduces the portion of dead space attributable to variations and barrel and hub tolerances. However, unlike the locking luer type fittings that become tighter as additional torque is applied to the needle hub, syringe assemblies having flat and low angle seals reach a sealed condition in a rather abrupt fashion due to their geometry.

When syringes and needle assemblies of any of the above-mentioned geometries are assembled in the manufacturing facility, the needle assembly can be attached to the syringe barrel using an optimal amount of torque applied to the needle hub therefore avoiding needle hubs that are not properly attached which can lead to leaking of medication and needle hubs which are over tightened which can have long term consequences due to creep in the plastic components which relax over time and lose their preload. However, in a clinical setting the attaching of a needle assembly to a syringe barrel is not done with the consistent controlled force found in the manufacturing process. Some users of the syringe and needle assembly are strong, some are weak and many have their own preconceived opinion regarding what the proper torque needed to attach a needle assembly.

Although the prior art teaches many syringe barrel and needle hub connecting structures, there is still a need for a low dead space syringe which will not attach the needle assembly to the syringe barrel unless an adequate amount of torque is applied to the needle hub and which will not tighten further after proper installation has occurred.

SUMMARY OF THE INVENTION

A syringe and detachable needle assembly having binary attachment features includes an elongate syringe barrel having a longitudinal axis, an inside surface defining the chamber for retaining fluid, an open proximal end and an open distal end including a collar. A portion of the collar includes a cylindrically shaped sidewall having an inside surface and an outside surface. A needle assembly includes a hub having a body portion including a proximal end, a distal end and a conduit therethrough. The needle assembly further includes a cannula having a distal end, a proximal end and a lumen therethrough. The proximal end of the cannula is connected to the distal end of the hub so that the lumen is in fluid communication with the chamber in the barrel. A lug on one of said collar and said hub, and a ramp and a rest surface on the other of said collar and said hub. The ramp is oriented at an acute angle with respect to the longitudinal axis for guiding the lug during needle assembly attachment, to the rest surface forcing the hub to contact the barrel to form a seal between the hub and the barrel. Rotation of the hub with respect to the barrel is less than 180° when the lug travels along the ramp during installation of needle assembly to the barrel.

The syringe assembly may further include a distally facing annular surface projecting inwardly from the open proximal end of the barrel and a proximally facing annular surface on the body portion of the hub contacting the distally facing annular surface to form a seal between the hub and the barrel.

The proximally facing annular surface on the hub may be in the form of a flexible annular skirt.

The hub is preferably loosely retained by the barrel during most of the travel of the lug along the ramp so that during this time the hub is not sealed to the barrel and an attempt to remove the needle shield in an axial direction will cause the hub to become disconnected from the barrel.

The syringe assembly may include a discontinuity between the ramp and the rest surface for providing additional tactile feedback to the user during rotation of the needle assembly with respect to the barrel as the lug transitions from the ramp to the rest surface. The discontinuity may provide additional resistance to the movement of the lug as it transitions from the ramp to the rest surface. The discontinuity may also increase the length of the ramp so that the lug moves slightly farther proximally with respect to the collar before falling back onto the rest surface.

The syringe assembly may include a projection on the hub configured for contacting a protuberance on the collar for providing additional tactile feedback to the user during rotation of the needle assembly with respect to the barrel as said lug transitions from said ramp to said rest surface.

The syringe assembly of the present invention is preferably configured so that the hub is loosely retained by the barrel during most of the travel of the lug along the ramp so that an attempt to remove the needle shield in an axial direction results in the hub becoming disconnected from the barrel.

The syringe assembly may include four lugs and the ramp may include two ramps with two rest surfaces. It is also desirable to have rest surfaces without ramps, e.g., two opposed ramps with rest surfaces and two opposed rest surfaces without ramps.

The syringe assembly is preferably configured so that the rotation of the hub with respect to the barrel is less than 100° while the lug travels along the ramp during installation of the needle assembly to the barrel.

The body portion of the hub may also include an outwardly projecting annular sealing ring for sealing engaging the sidewall of the collar to form a seal between the hub and barrel. The sealing ring may take the form of an elastomeric o-ring. The annular sealing ring may be integrally formed with the body portion of the hub. Further, the annular sealing ring may be configured to be a tapered projection having a base adjacent to the body portion of the hub and a free-end wherein the tapered projection is wider at its base than at its free-end.

The syringe assembly may further include an elongate plunger rod having a proximal end, a distal end and a stopper at the distal end slidably positioned in fluid tight engagement with the inside surface of the barrel for displacing fluid from the chamber through the cannula by relative motion of the plunger rod with respect to the barrel. The stopper may also include a distally facing projection for the partially occluding the conduit in the needle hub when the stopper is in its distal most position inside the barrel.

The needle assembly may also include an elongate hollowed needle shield having a distal end and an open proximal end removably engaging the hub so that the needle covers the cannula.

The cannula may be integrally formed with the hub using thermoplastic material. Further the cannula may have a sharp or a blunt tip.

The syringe assembly of the present invention may be configured so that a lug projects outwardly from the body portion of the hub and a ramp is in the inside surface of the sidewall of the barrel collar.

The syringe assembly may be configured so that a lug projects inwardly from the body portion of the hub and a ramp is formed on the outside surface of the sidewall of the collar of the barrel.

The syringe assembly may be configured so that the lug projects inwardly from the inside surface of the sidewall of the collar and the ramp is formed on the exterior of the body portion of the hub.

The syringe assembly may be configured so that a lug projects outwardly from the outside surface of the sidewall of the collar of the barrel and a ramp is formed on the inside of the body portion of the hub.

A rest surface may include a portion of the periphery of an aperture through the sidewall of the barrel collar.

Another embodiment of the present invention includes a syringe and detachable hub having binary attachment features including an elongate syringe barrel having a longitudinal axis, an inside surface defining a chamber for retaining fluid, an open proximal end, an open distal end including a collar, and a portion of the collar including a cylindrically shaped sidewall having an inside surface and an outside surface. A hub has a body portion including a proximal end and a distal end. A lug on one of the collar or the hub, and a ramp and a rest surface on the other of the collar or the hub are provided. The ramp is oriented at an acute angle with respect to the longitudinal axis for guiding the lug, during hub attachment, to the rest surface forcing the hub to contact the barrel to form a seal between the seal between the hub and the barrel. The rotation of the hub with respect to the barrel is desirably less than 180° and preferably less than 100° while the lug travels along the ramp during installation of the hub to the barrel. It is not necessary that the hub have a conduit therethrough in fluid communication with the chamber in the barrel. The hub without a conduit therethrough or with an occluded conduit can function as a cap to seal medication in the syringe assembly of the present invention before the time of use. Also, the syringe of the present invention can be used with the needle assembly for filling the syringe with medication using an appropriately sized cannula. After filling, the cannula is discarded and a hub, without a conduit, is attached to the distal end of the barrel to seal in and protect the medication. At the time of use, the hub is removed and a needle assembly having a cannula, appropriately sized for injection, is attached to the barrel.

The present invention also includes a method of making an elongate syringe barrel for use with a needle assembly having a hub wherein the hub includes a body portion having an outwardly projecting lug and a proximally facing annular surface. The barrel includes a longitudinal axis, an outside surface and an inside surface defining a chamber for retaining fluid, an open proximal end, an open distal end including a collar and a distally facing annular surface projecting into the open proximal end. A portion of the collar includes a cylindrically shaped sidewall having an inside surface and an outside surface. A ramp and a rest surface project inwardly from the inside surface of the collar. The ramp is oriented at an acute angle with respect to the longitudinal axis for guiding the lug, during needle attachment, to the rest surface forcing the annular surface on the hub to contact the annular surface in the open proximal end of the barrel to form a seal between the hub and the barrel. The rotation of the hub with respect to the barrel is desirably less than 180° and preferably less than 100° while the lug travels along the ramp during installation of needle assembly to the barrel. The method of molding comprises the steps of: providing an injection mold having a cavity defining a syringe barrel. The mold includes a fixed portion defining the outside surface of the barrel, a proximal core pin defining the chamber in the barrel, a split cavity defining the outside surface of the collar and including a raised projection for forming an aperture in the collar, the ramp and the rest surface, and a straight-pulled distal core pin defining the remaining portions of the interior of the collar. The distal core pin contacts the raised surface on the split cavity when the mold is closed. The method further includes injecting molten thermoplastic material into the cavity of the mold; allowing enough time for the thermoplastic material to solidify enough to allow movement of the barrel with respect to the mold; opening the split cavity so that the raised projection is outside of the collar; and removing the proximal core pin and the barrel axially from the fixed portion of the mold without rotation of the distal core pin.

The method of the present invention further including the raised projection on the split cavity being further configured to cooperate with the distal core pin to form a guide surface running along and spaced from the ramp, for guiding the lug during removal of the needle assembly from the barrel.

A method of the present invention may further include the split cavity having a second projection and the core pin is configured to cooperate with the second projection of the split cavity to form an additional aperture in the collar and an additional rest surface. Distal core pin is configured for defining the remaining portions of the additional rest surface. The additional rest surface does not have a ramp for guiding a lug connected to it.

The method is preferably carried out with thermoplastic materials selected from the group consisting of polypropylene, polyethylene, polycarbonate, PET and combinations thereof.

DETAILED DESCRIPTION

Figure 1:
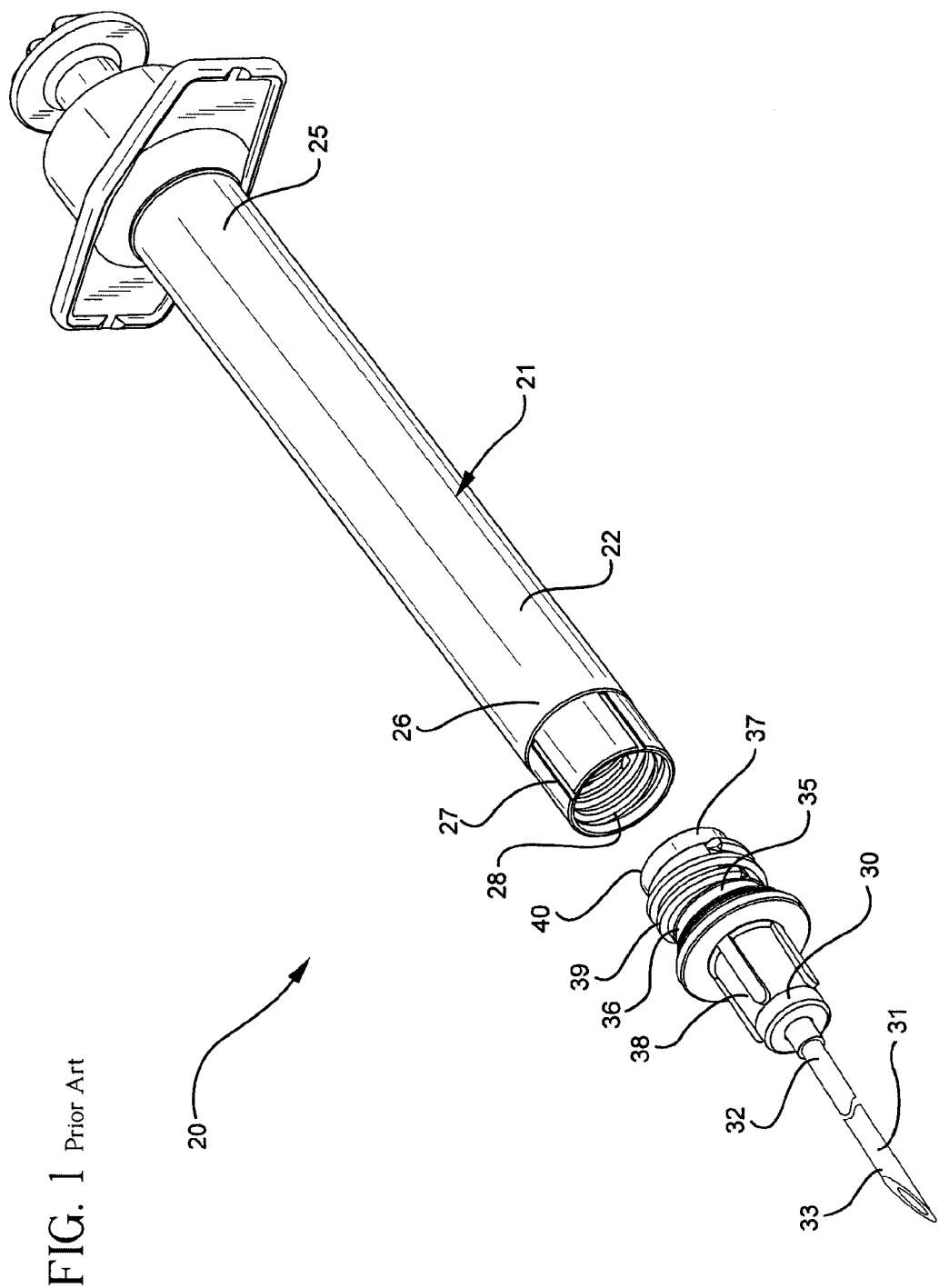
FIG. 1 is an exploded perspective view of a prior art needle assembly and syringe.

While this invention is satisfied by embodiments in many different forms, there are shown in the drawings and will herein be described in detail, preferred embodiments of the invention with the understanding that the present disclosure is to be considered exemplary of the principles of the invention and not intended to limit the invention to the embodiments illustrated. The scope of the invention will be measured by the appended claims and their equivalents.

Figure 2:
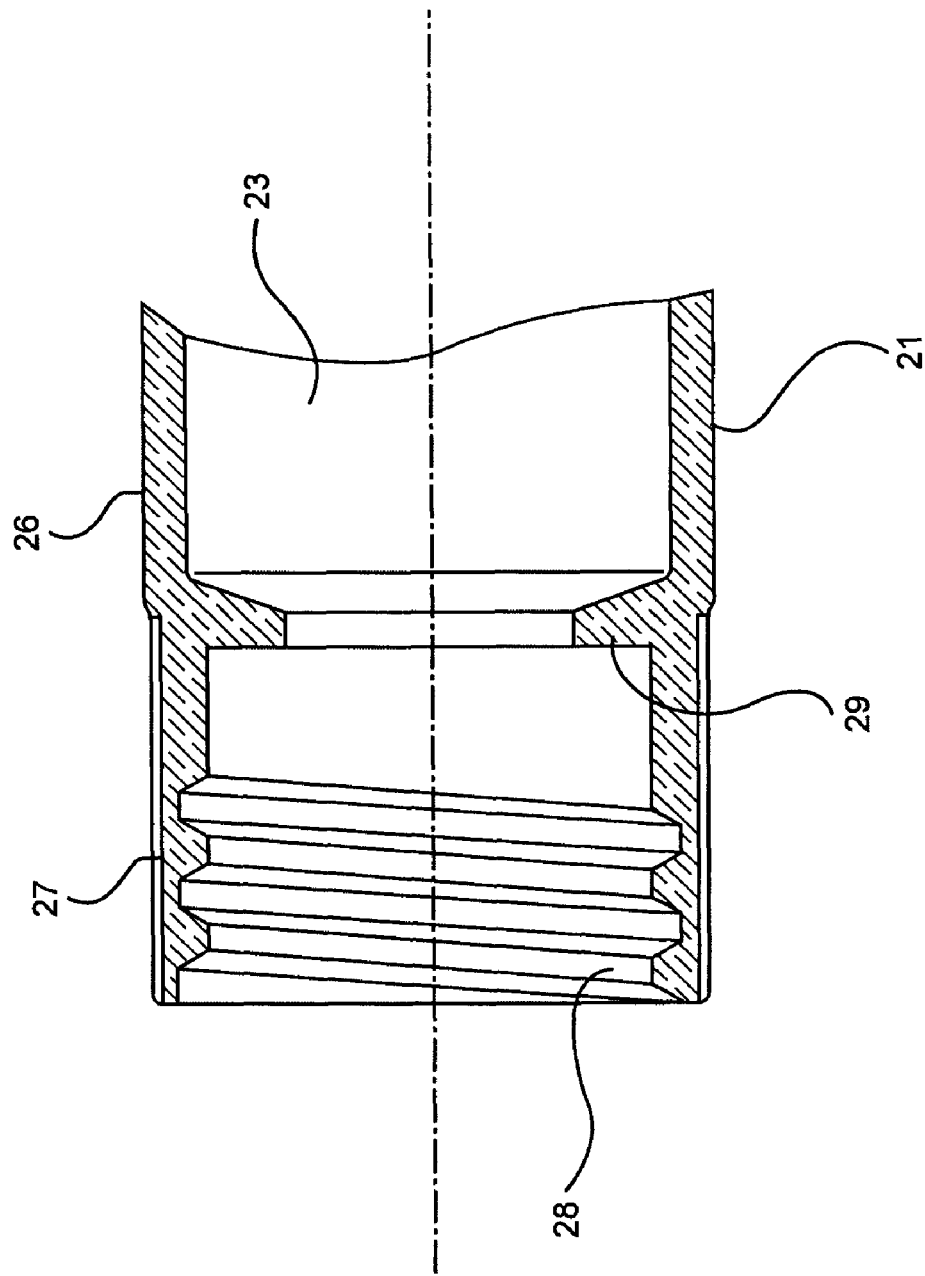
FIG. 2 is an enlarged cross-sectional view of the distal end of the syringe barrel of FIG. 1.
Figure 3:
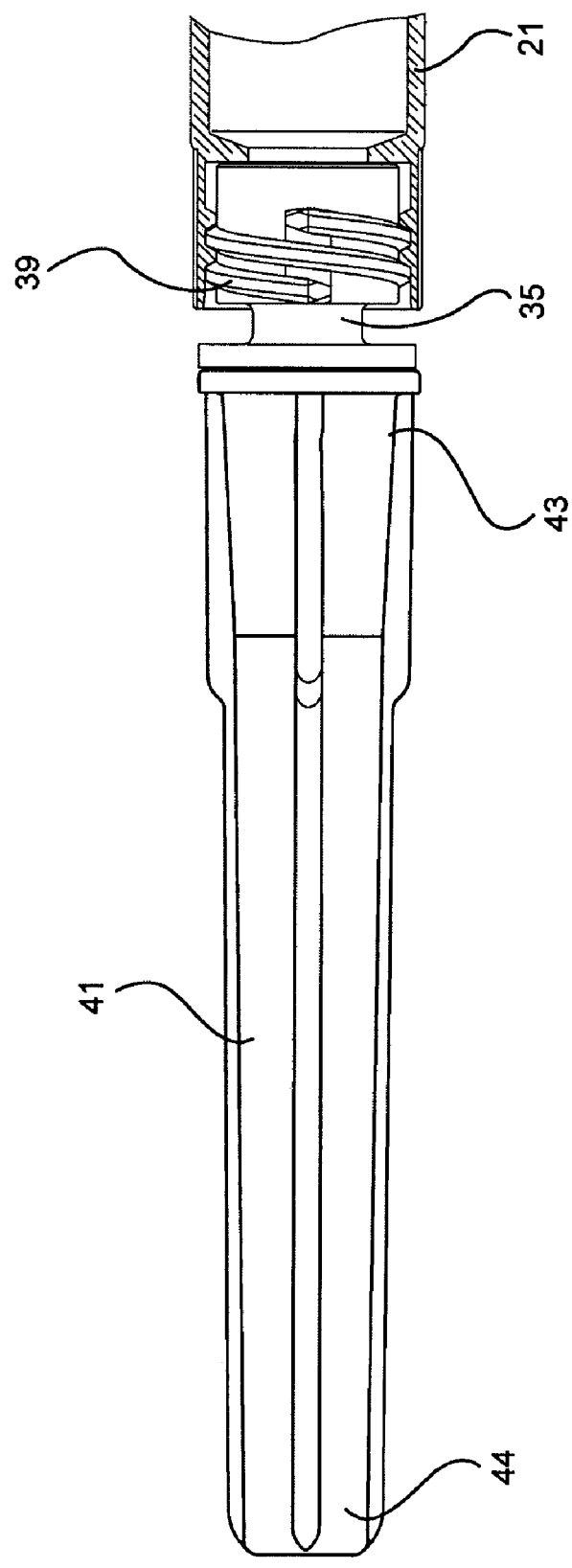
FIG. 3 is a partial cross-sectional view showing a needle assembly of FIG. 1 attached to the syringe barrel of FIG. 1.
Figure 4:
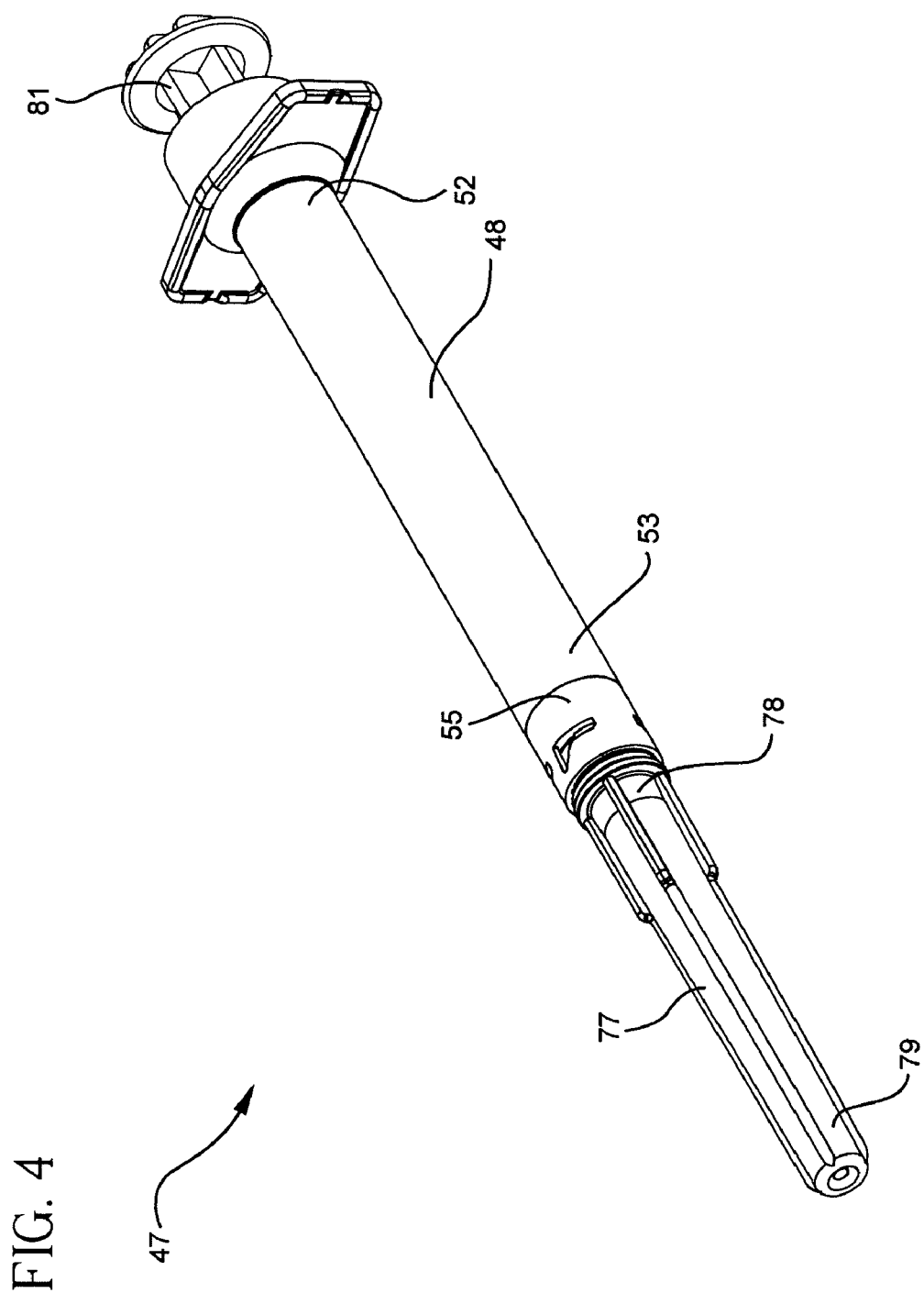
FIG. 4 is a perspective view of a syringe and removable needle assembly of the present invention.
Figure 5:
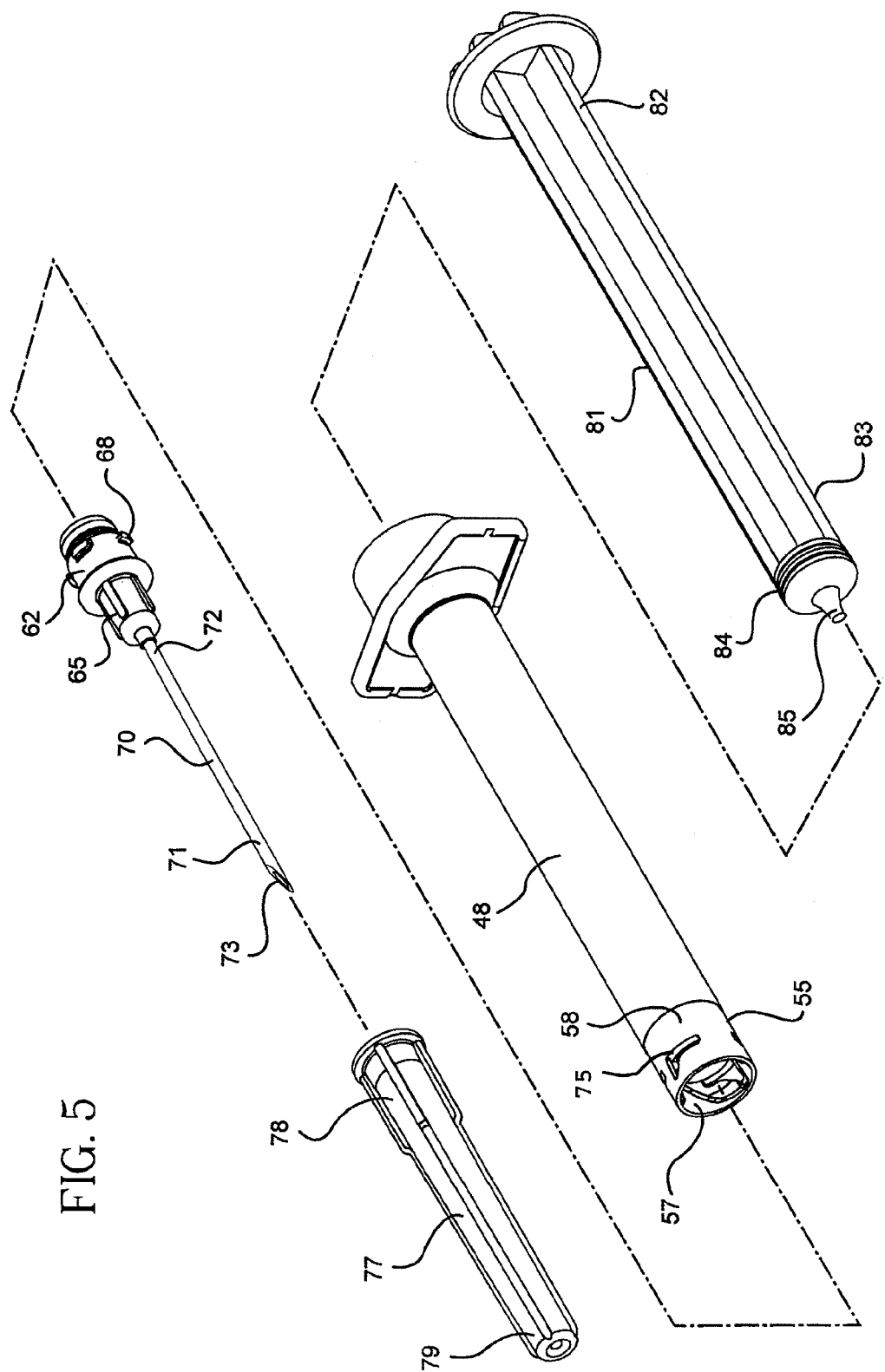
FIG. 5 is an exploded perspective view of the components of the syringe assembly of FIG. 4.
Figure 6:
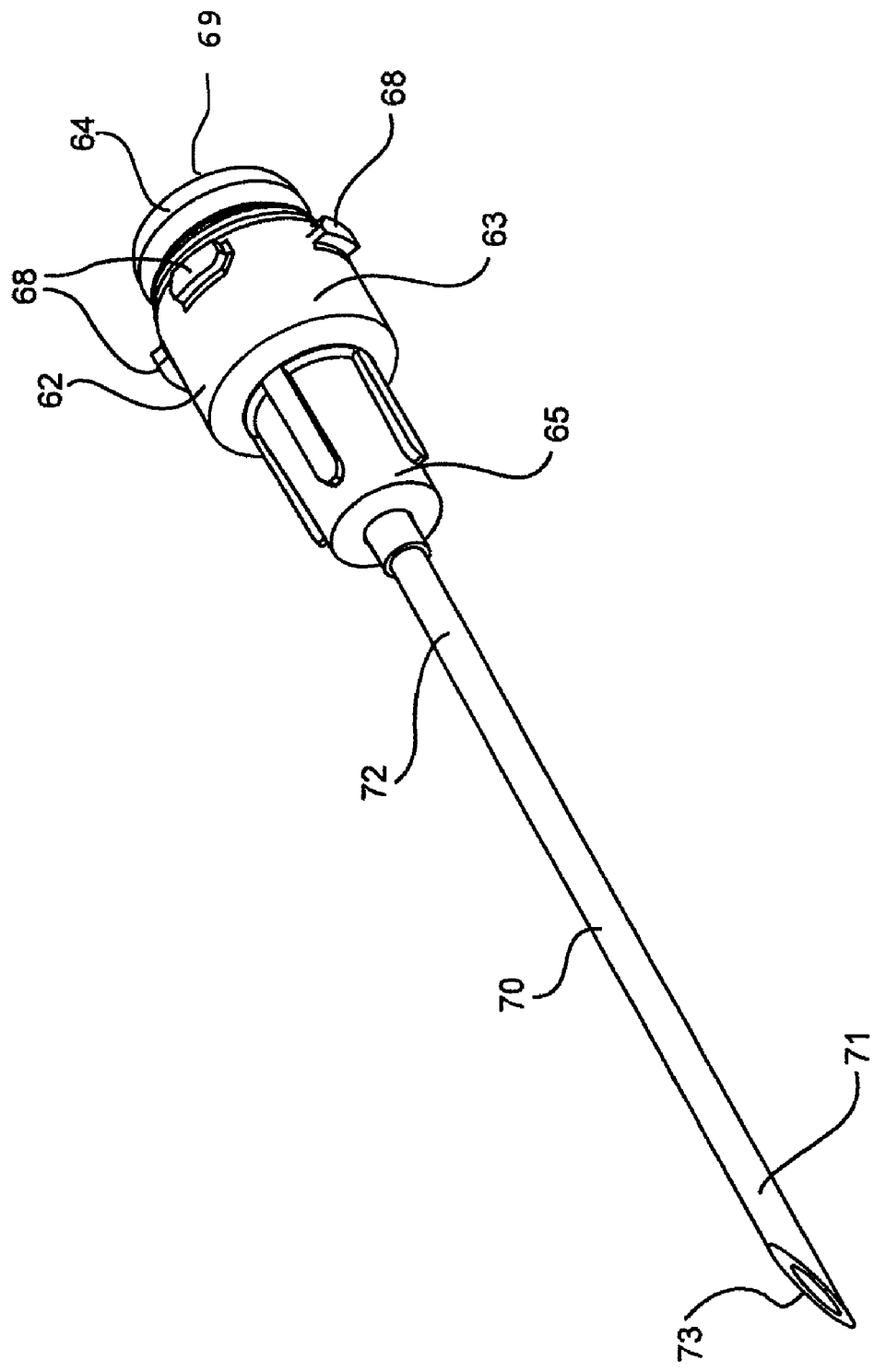
FIG. 6 is a side-elevational view of the hub of the needle assembly.

Referring to FIGS. 1-3, a prior art syringe assembly 20 includes a barrel 21 having an elongate body 22 defining a chamber 23 for retaining fluid. The barrel includes an open proximal end 25, an open distal end 26 including a collar 27 having an internal thread 28 therein. The barrel also includes an annular sealing surface 29.

A prior art needle assembly 30 includes a cannula 31 having a proximal end 32, and distal end 33 and a lumen (not shown) therethrough. A hub 35 includes a body portion 36 having a proximal end 37 and a distal end 38, a passageway therethough. The body portion further includes an external thread for mating engagement with the thread in the barrel collar and an annular sealing surface 40 positioned for contacting sealing surface 29 of the barrel.

A hollow needle shield 41 includes an open proximal end 43 and a distal end 44. The open proximal end of the needle shield frictionally engages the body portion of the needle hub. The needle shield is provided to protect the cannula during handling and attaching the needle assembly to a syringe barrel at which time it is removed so that the needle and syringe can be used for their intended purpose.

Attaching the needle assembly to the barrel involves placing the proximal end of the needle hub body in the barrel collar and rotating the needle assembly so that the thread on the needle assembly engages the thread in the barrel collar. Continued rotation closes the hub to enter the collar in a distal direction and continue moving in that direction until the annular sealing surface 40 on the hub contacts annular sealing surface 29 in the barrel. Additional rotation will render the interface of the two annular sealing surfaces fluid tight.

The most common prior art needle hub and syringe connection (not shown) involves a frusto-conically shaped tip on the syringe barrel which engages a frusto-conically shaped recess in the hub. During installation the rotational forces required increase as the frusto-conically shaped tip frictionally engages the corresponding recess in the hub. In the embodiment illustrated, the transition from relatively unrestricted rotation to sealing is more abrupt. If the user does not provide enough additional torque after the sealing surfaces have contacted, the syringe and needle assembly may leak fluid during the injection process. Excessive force can damage the fitting or over-stress the fitting so that it may be compromised over time. A good analogy to the present situation is the commonly available machine screw and threaded nut assembly. Without a torque wrench to facilitate the installation, it is left up to the common sense and experience of the user. In the minority of cases, some users do not tighten the screw and nut enough and it subsequently becomes loose or, in the alternative, the user over tightens the combination until the threads are stripped and the connection becomes inoperable.

The present invention overcomes this problem by providing a syringe and needle assembly that limits the amount of torque that can be applied when attaching a needle assembly to a barrel and provides feedback to the user indicating that proper installation has occurred. Thus providing a uniform sealed connection between the needle assembly and the barrel over a wide range of users both weak and strong and experienced and inexperienced.

Referring to FIGS. 4-7, a syringe and removable needle assembly 47 having binary attachment features includes an elongate syringe barrel 48 having a longitudinal axis 49, an inside surface 50 defining a chamber 51 for retaining fluid, an open proximal end 52, an open distal end 53 including a collar 55. A portion of the collar includes a cylindrically shaped sidewall 56 having an inside surface 57 and an outside surface 58.

Needle assembly 61 includes a hub 62 having a body portion 63 including a proximal end 64, a distal end 65 and a conduit therethrough. The needle assembly further includes a cannula 70 having a distal end 71, a proximal end 72 and a lumen 73 therethrough. The proximal end of the cannula is connected to the distal end of the hub so that the lumen of the cannula is in fluid communication with the chamber in the barrel. The cannula may be integrally formed with the hub as by injection molding using thermoplastic materials or separately formed, as in this embodiment, and attached to the hub.

In this embodiment, adhesive 74 is used to attach the cannula to the hub, and the cannula is made of metal, preferably stainless steel.

The present invention contains structural and functional features that to avoid the use of excessive torque when attaching the needle assembly to the syringe barrel and feedback features so the user knows when the needle assembly is properly attached to the barrel. In particular, the present invention includes at least one lug on the collar or on the hub and a ramp and a rest surface on the other of the collar or the hub. When attaching a needle assembly to a syringe barrel the lug moves along the ramp until it reaches the rest surface which prevents the needle assembly from being secured more tightly than it is at this point.

In this preferred embodiment, body portion 63 of hub 62 includes an outwardly projecting lug and inside surface 57 of collar 55 includes a ramp 59 positioned at an acute angle with respect to the longitudinal axis of the barrel. The ramp terminates in a rest surface 60 which is preferably, but not necessarily, in a plane perpendicular to the longitudinal axis of the barrel. Collar 55 includes an aperture 75 therethrough. The rest surface includes a portion of the periphery of the aperture. Formation of this aperture will be discussed in more detail herein after.

When attaching the needle assembly to the barrel, the user positions the proximal end of the hub inside the collar and rotates the hub with respect to the barrel so that lug 68 travels along ramp 59. The hub moves into the collar sealing the hub and the barrel against leakage, at which time, the lug transitions from the ramp to the rest surface. At this point, the user experiences a reduction in the amount of torque necessary to rotate the hub with respect to the barrel which is a sign that the needle assembly is properly attached to the barrel. In this preferred embodiment, the structure provided for sealing the hub to the barrel includes a distally facing annular surface 76 projecting inwardly into the open proximal end of the syringe barrel. A proximally facing annular surface 69 on body portion 63 of the hub is positioned for contacting distally facing annular surface 76 of the barrel to form a seal between the hub and barrel and prevent leakage during the injection process. It should be noted that proximally facing annular surface 69 on the hub and distally facing annular surface 76 in the barrel need not be aligned exactly at 90° from the longitudinal axis. A broad range of angles will work with the angles of 88° to 92° being desired, and 90° being preferred.

The rotation of the hub with respect to the barrel during the attachment process, while the lug travels along the ramp results in a rotation of the needle assembly of less than 180° with respect to the barrel and preferably less than 100°. When the lug transitions onto the rest surface, further rotation of the hub with respect to the barrel will not result in a substantial additional tightening of the seal between the hub and the barrel.

Another important feature of the present invention is that the hub is loosely retained by the barrel during most of the travel by the lug along the ramp so that the syringe and needle assembly are incapable of injecting fluids without leaking fluid outside the lumen until the lug is positioned on the rest surface. This retention during the movement of the lug along the ramp may be so slight that the needle assembly could easily become disengaged from the barrel further alerting the user to the fact that the needle assembly is not properly attached. Syringe assemblies having threaded connections between the needle hub and the barrel do not have this feature.

The syringe assembly may also include an elongate plunger rod 81 having a proximal end 82, a distal end 83 and a stopper 84 at the distal end of the plunger rod. The stopper is slidably positioned in fluid tight engagement with inside surface 50 of the barrel for dispensing fluid from the chamber through the cannula by relative motion of the plunger rod with respect to the barrel. The stopper desirably includes a distally facing projection 85 for partially occluding the distal end of the barrel when the stopper is in its distal most position inside the barrel to reduce dead space.

Figure 7:
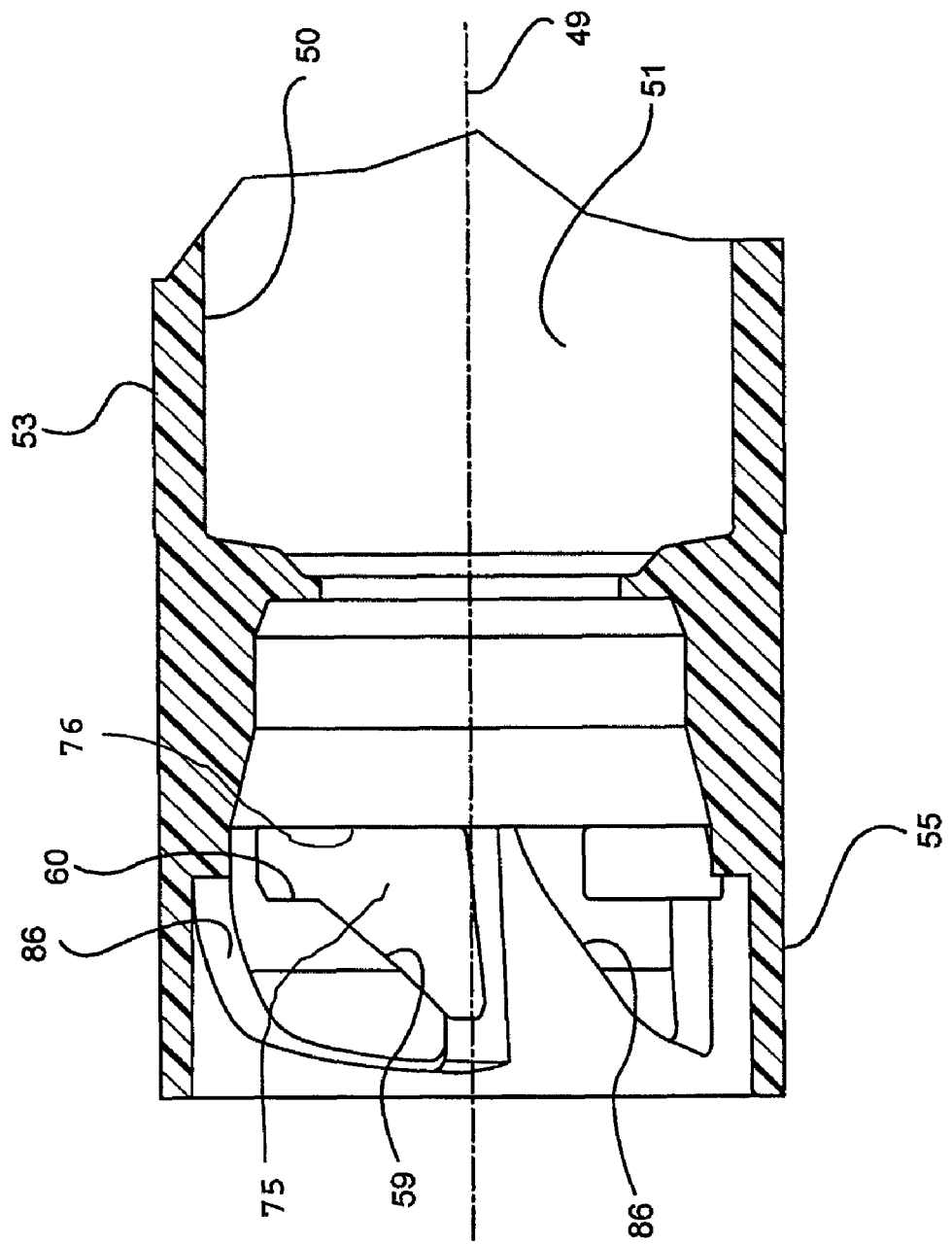
FIG. 7 is an enlarged cross-sectional view of the distal end of the syringe barrel of FIG. 5.

As best illustrated in FIG. 7, the collar includes a guide surface 86 running along and spaced from ramp 59 for guiding the lug during removal of the needle assembly from the barrel. This feature is not necessary to practice the present invention but is preferred since the guide surface also helps align the lugs during attachment of the needle assembly to the syringe barrel.

Figure 8:
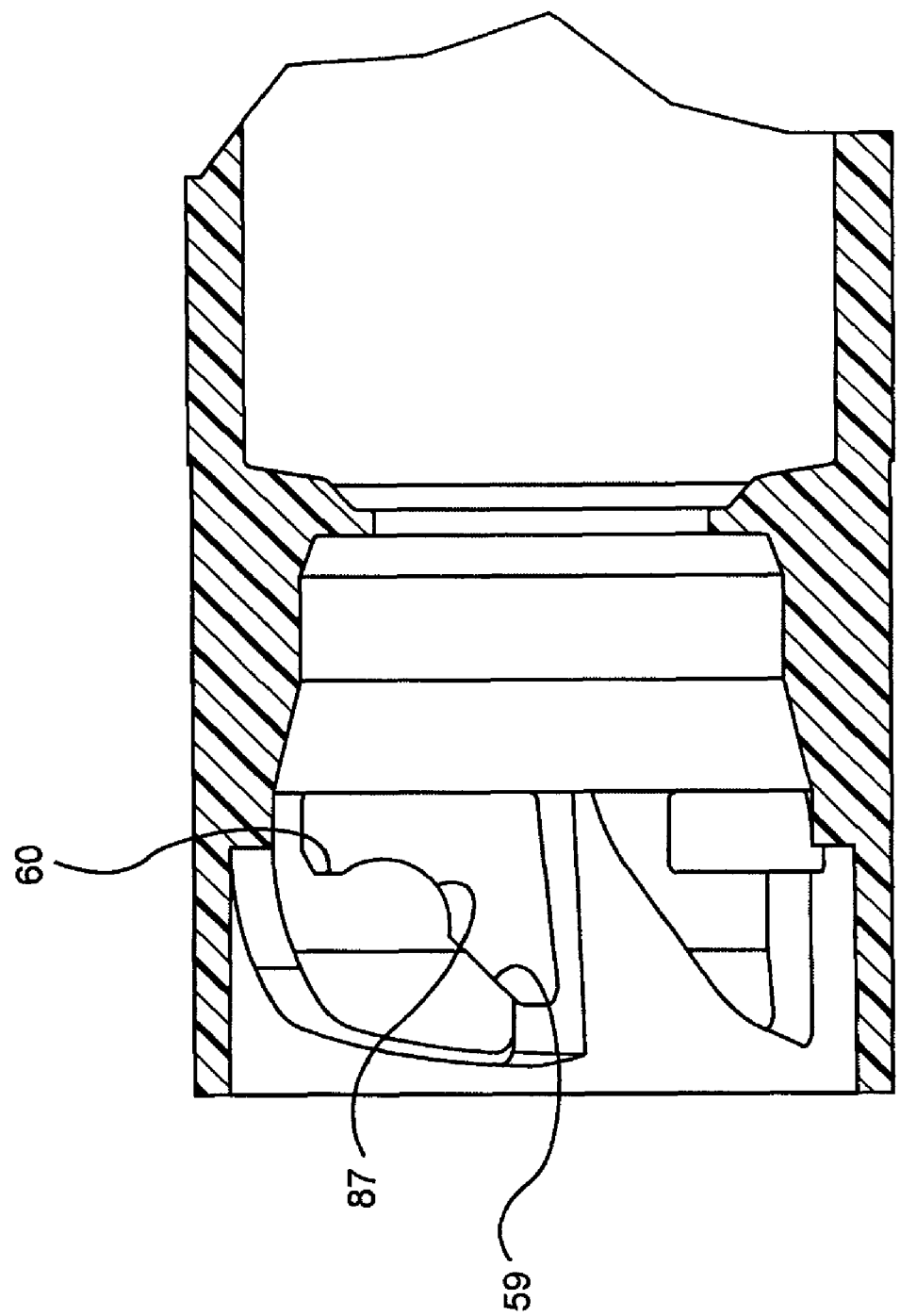
FIG. 8 is an enlarged cross-sectional view of the distal end of an alternative syringe barrel structure.

It is also within the purview of the present invention to include a discontinuity between the ramp and the rest surface for providing additional tactile feedback to the user during rotation of the needle assembly with respect to the barrel as the lug transitions from the ramp to the rest surface. Such a discontinuity is illustrated as element 87 in FIG. 8 as the lug travels up ramp 59 to rest surface 60, its path is interrupted by discontinuity 87 which, in this configuration, increases the amount of torque necessary to rotate the needle hub with respect to the barrel until the lug travels over the discontinuity and falls onto rest surface 60. The discontinuity can take many configurations. Here discontinuity 87 lengthens the travel of the lug to the rest surface, however, this is not necessary and any form of detent which is detectable by the user through touch and/or audible feedback is within the purview of the present invention and discontinuity 87 is merely representative of these many possibilities.

Figure 10:
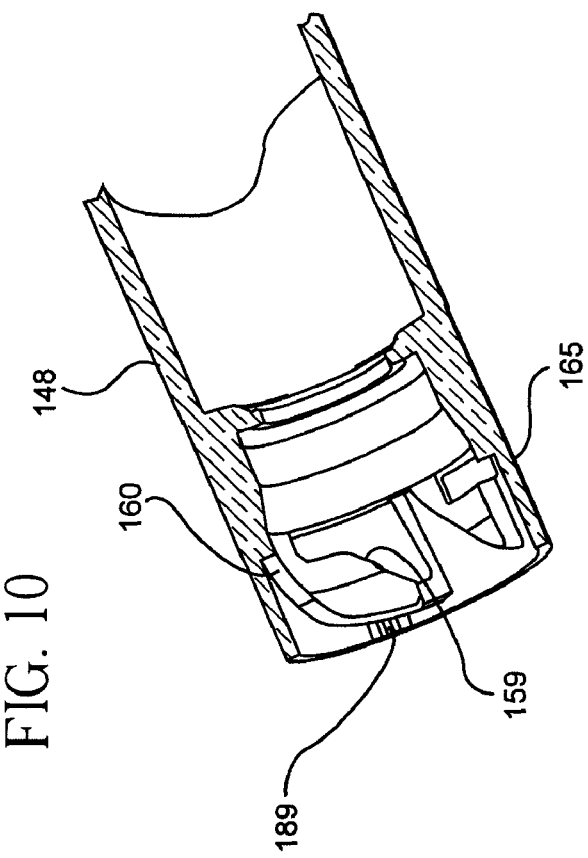
FIG. 10 is a cross-sectional view of the distal end of a syringe barrel for use with the needle assembly of FIG. 9.
Figure 9:
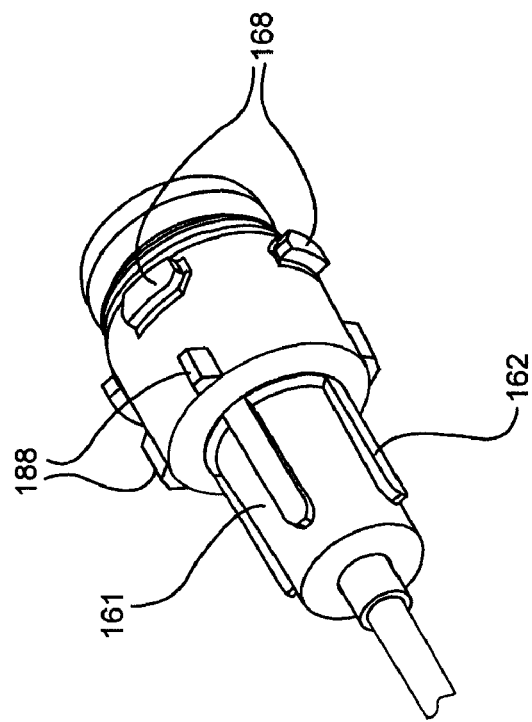
FIG. 9 is a side-elevational view of alternative needle assembly of the present invention.

FIGS. 9 and 10 illustrate another structure for providing tactile feedback to the user during rotation of a needle assembly 161 with respect to a barrel 148 as a lug 168 transitions from a ramp 159 to a rest surface 160. In this embodiment, a projection 188 on hub 162 engages a protuberance 189 on collar 155 of the syringe barrel at the approximate angular position where the lug is transitioning from ramp 159 to rest surface 160. This feature provides tactile feedback to the user that the needle assembly is properly attached to the barrel and no further twisting action is required. This feature also provides resistance to accidental or unintentional removal of the needle assembly. Also, the structure in this embodiment does not modify the ramp and rest surface configuration so that each function can be optimized without affecting the other. There are many combinations of projections and protuberances on the hub and barrel for accomplishing this result and the outwardly projection 188 and the recessed protuberance 189 illustrated in FIGS. 10 and 11 are merely representative of these many possibilities, all of which are within the purview of the present invention.

Figure 11:
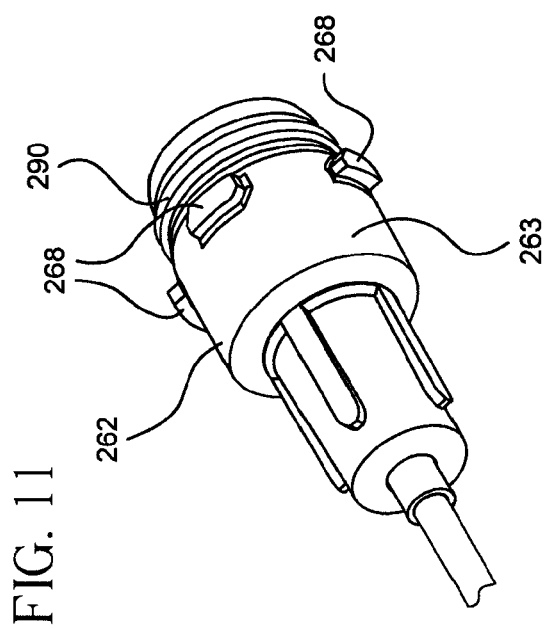
FIG. 11 is a side-elevational view of another alternative needle assembly of the present invention.
Figure 12:
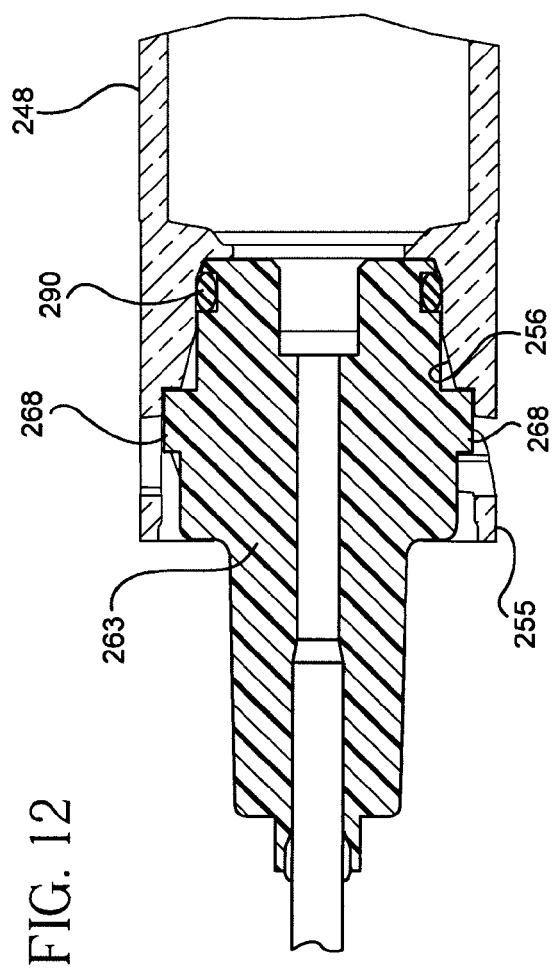
FIG. 12 is a cross-sectional view of the needle assembly of FIG. 11 attached to a syringe barrel.

FIGS. 11 and 12 illustrate another alternative embodiment of the present invention. This embodiment hub 262 includes a body portion 263 having a plurality of lugs 268 extending outwardly therefrom. Syringe barrel 248 includes a collar 255 having an inside surface 256. Body portion 263 of the hub further includes an outwardly projecting annular sealing ring 290 which in this embodiment is an elastomeric o-ring. When the needle assembly is attached to the syringe barrel, outwardly projecting annular sealing ring 290 engages inside surface 256 of the collar to form a seal between the hub and the barrel to help prevent leakage of the contents of the barrel through the space between the hub and the barrel.

Figure 13:
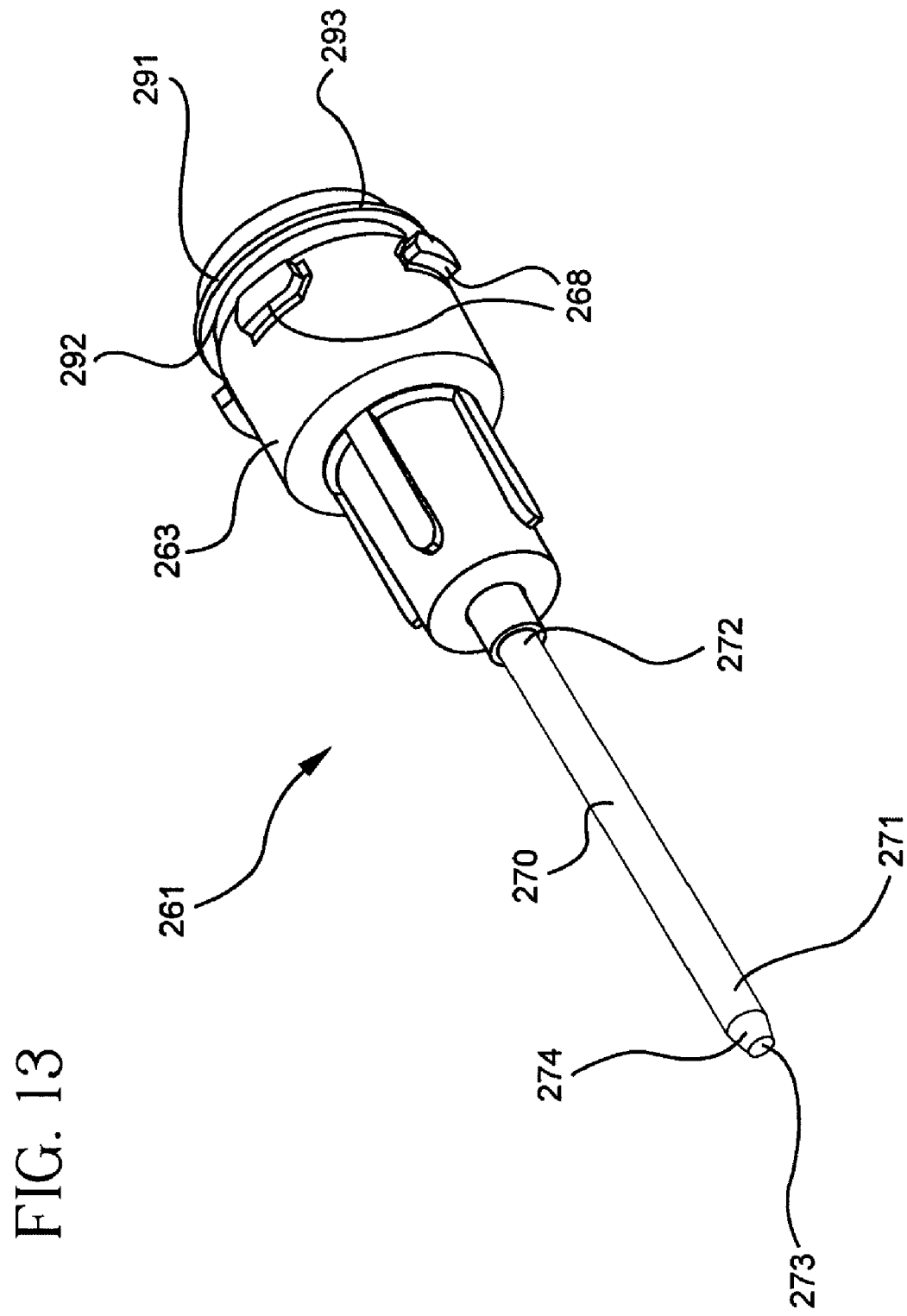
FIG. 13 is still another alternative needle assembly similar to the needle assembly of FIG. 11.
Figure 14:
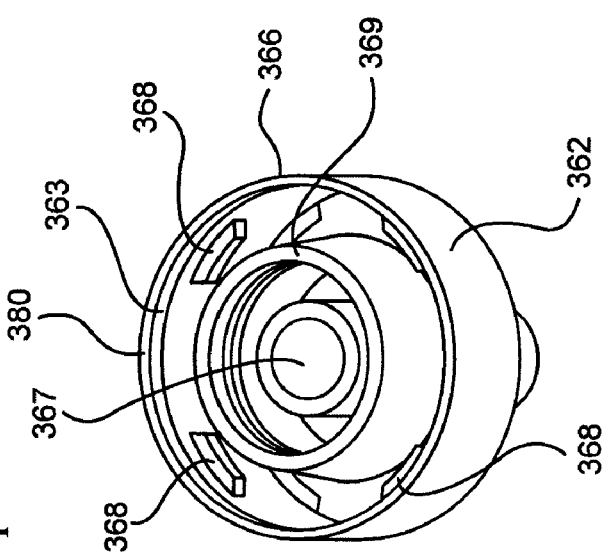
FIG. 14 is perspective view of the distal end of an alternative syringe barrel of the present invention.

FIG. 13 illustrates a needle assembly 261 having an alternative outwardly projecting sealing ring 291 on a hub that is similar to the hub of FIG. 11. In this embodiment, outwardly projecting annular sealing ring 291 is integrally formed with the body portion of the hub for sealing engagement with the inside surface of the collar to form a seal between the hub and the barrel. In this embodiment, annular sealing ring 291 is a tapered projection having a base 292 adjacent to body portion 263 of the hub and a free-end 293. The tapered projection is preferably wider at its base than at its free-end. A wide variety of materials and structures can be used to form an annular sealing ring and the structures illustrated in FIGS. 12-14 are merely representative of these many possibilities, all of which are in the purview of the present invention. Needle assembly 261 further includes a cannula 270 having a distal end 271, a proximal end 272 and a lumen 273 therethrough. Hub body portion 263 and cannula 270 are integrally formed of thermoplastic material. Cannula 270 further includes a blunt distal tip 274 rather than a sharp distal tip as illustrated in the embodiment of FIGS. 4-7.

Figure 15:
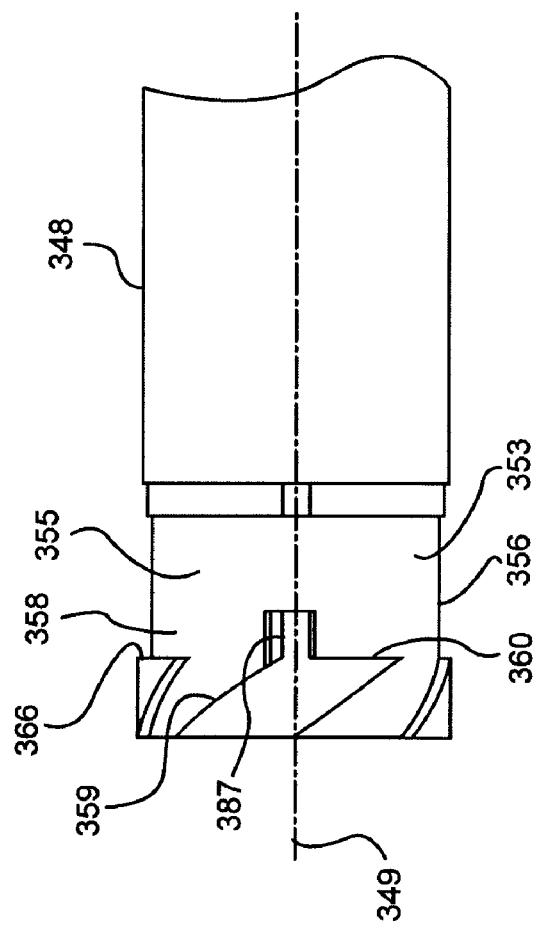
FIG. 15 is a perspective view of a needle hub for use with the syringe barrel of FIG. 14.

FIGS. 14 and 15 illustrate another alternative embodiment of the present invention. In this embodiment syringe barrel 348 includes an open distal end 353 having a collar 355 wherein a portion of the collar includes a cylindrically shaped sidewall 356 having an outside surface 358. A needle assembly includes a hub 362 having a body portion 363 including a conduit 367 therethrough, an annular collar 366 preferably having four lugs 368 on its interior surface. Outside surface 358 of collar 355 preferably includes two ramps 359 and a rest surface 360 associated with each ramp. Additional rest surfaces 366 may be provided without ramps. The ramp is oriented at an acute angle with respect to longitudinal axis 349 of the barrel, for guiding lugs 368 during needle assembly attachment, to rest surfaces 360. Hub 362 includes proximally facing annular sealing surface 369 including an annular proximally facing skirt 308. The annular proximally facing skirt contacts a distally facing annular sealing surface in the barrel when the needle assembly is properly installed. The inclusion of an annular proximally facing skirt provides a more flexible surface on the hub for improving the quality of seal between the hub and the distally facing annular surface of the barrel.

A syringe and needle assembly of this embodiment functions similarly to the previous embodiments in that the lug travels along the ramp during installation of the needle assembly to the barrel which is complete when the lug rests on rest surface 360. Also included in this embodiment, is a discontinuity for providing additional resistance to the movement of the lug as it transitions from the ramp to the rest surface. Also this discontinuity is intended to provide additional resistance to the lugs when the needle assembly is being removed from the syringe barrel. In this embodiment it is preferred that the rotation of the hub with respect to the barrel be less than 100° while the lug travels along the ramp during installation of the needle assembly to the barrel. Further, the lug and the ramp structure are configured so that the hub is loosely retained by the barrel during most of the travel of the lug along the ramps so that the syringe and needle assembly are incapable of injecting fluid without leaking fluid outside of the lumen before the lug reaches the rest area.

Figure 17:
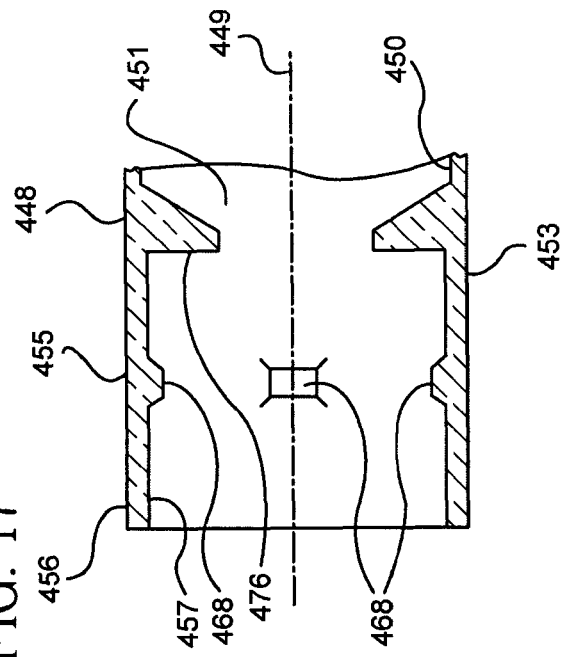
FIG. 17 is a cross-sectional view of the distal end of the syringe barrel for use with the needle assembly of FIG. 16.
Figure 16:
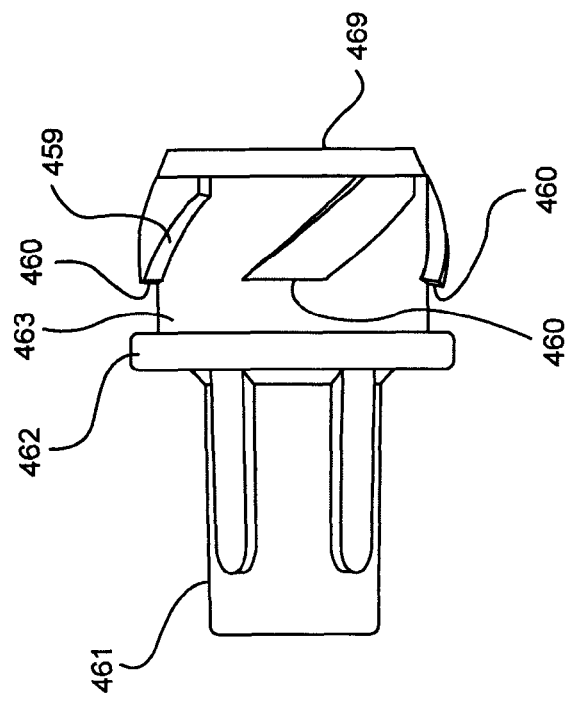
FIG. 16 is still another alternative needle assembly of the present invention.

FIGS. 16 and 17 illustrate still another embodiment of the present invention. This embodiment includes an elongate syringe barrel 448 having a longitudinal axis 449, an inside surface 450 defining a chamber 451 for retaining fluid, an open distal end 453 including a collar 455. A portion of the collar includes a cylindrically shaped sidewall 456 having an inside surface 457. Four lugs 468 are positioned equally distant along inside surface 457 and project inwardly. A needle assembly 461 includes a hub 462 having a body portion 463. Two outwardly projecting ramps 459 and four outwardly projecting rest surfaces 460 are equally spaced around the periphery of the body portion of the hub. In this embodiment, two of the lugs will move up two ramps during installation of the needle assembly and rest on the rest surfaces. The other two lugs will rest on rest surfaces 460 that do not have ramps. The syringe barrel includes a distally facing annular surface 476 projecting inwardly into the open proximal end of the barrel. The hub includes a proximally facing annular surface 469 for contacting the distally facing annular surface to form a seal between the hub and the barrel. This embodiment functions similarly to the embodiment of FIGS. 4-7.

Figure 18:
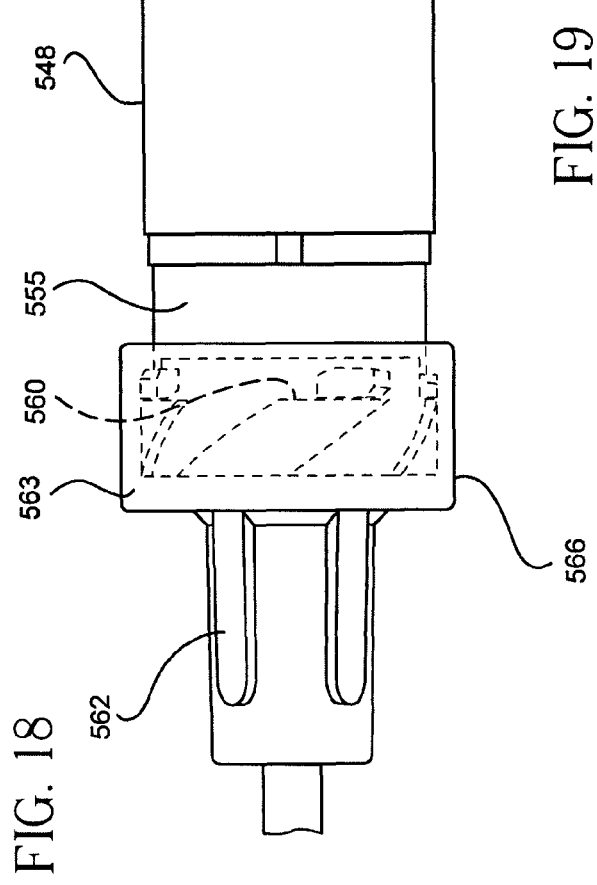
FIG. 18 is still another alternative embodiment of the needle assembly and syringe of the present invention.
Figure 19:
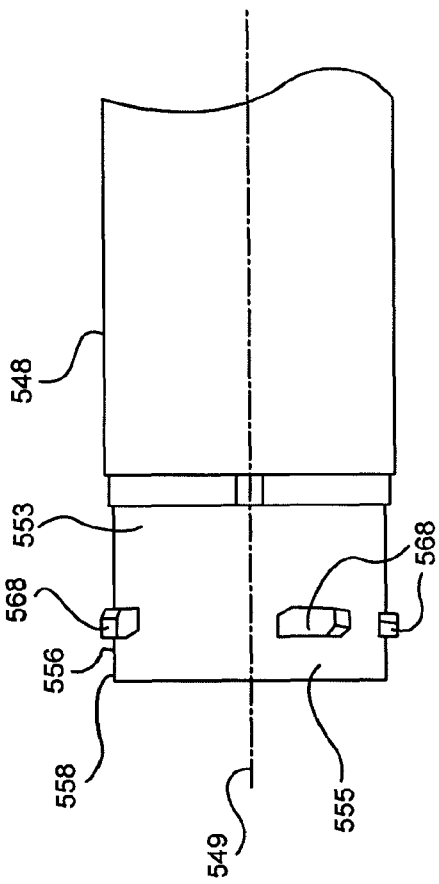
FIG. 19 is a side-elevational view of the syringe barrel of FIG. 18.

FIGS. 18 and 19 illustrate still another embodiment of the present invention. In this embodiment, an elongate syringe barrel 548 includes a longitudinal axis 549, an inside surface defining a chamber for retaining fluid, an open proximal end, and open distal end 553 including a collar 555. A portion of the collar includes a cylindrically shaped sidewall 556 having an outside surface 558. Four equally spaced lugs 568 are positioned on outside surface 558 of the collar. A needle assembly includes a hub 562 having a body portion 563. Body portion 563 includes an annular skirt 566 having an inside surface. At least two ramps are positioned on the inside surface and project inwardly. Each ramp terminates in a rest surface is preferably perpendicular to the longitudinal axis 549. This embodiment functions similarly to the embodiment of FIGS. 4-7. The needle assembly is attached to the syringe barrel through rotation of the hub which engages the lugs causing them to move along the ramps and onto the rest surfaces wherein the needle assembly is sealed to the barrel.

Figure 20:
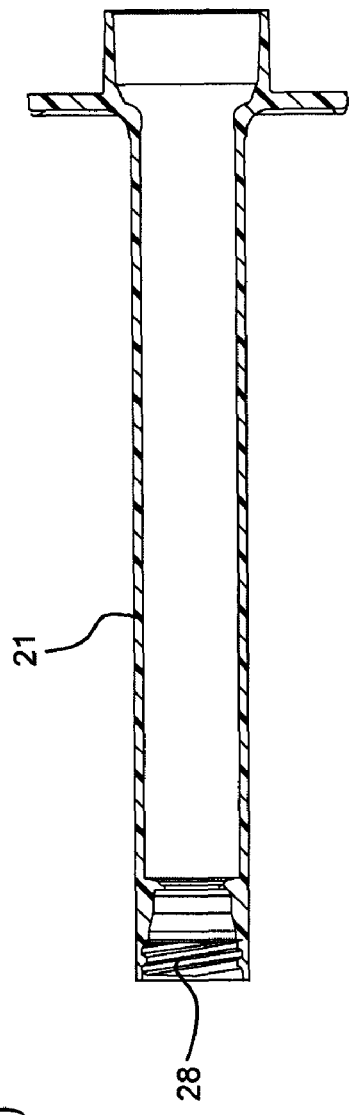
FIG. 20 is a cross-sectional view of the prior art syringe barrel.
Figure 21:
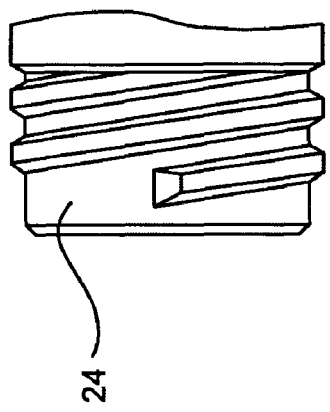
FIG. 21 is a side elevation view of a threaded core used to mold the syringe barrel of FIG. 20.

Referring to FIGS. 20 and 21, syringe barrels, such as barrel 21, are frequently made by injection molding. The process involves the use of a mold cavity and associated core pins that define an empty space in the shape of a syringe barrel. Molten plastic is injected into the space and solidifies through cooling to form the barrel. Thread cores, like thread core 24, are used to create threads in syringe barrels. The core is the negative of the internals of the desired part geometry. Once the part is molded, the thread core must be removed without smearing or damaging threads 28. This is achieved by unscrewing the thread core. This unscrewing action is driven by various gears, racks, hydraulics and/or motors depending on the mold design. This complexity adds cost to manufacture the mold. Also since the unscrewing action cannot be conducted concurrently with other mold actions such as opening and closing the mold press. Accordingly, the time to unwind the core adds to the process cycle time increasing the cost to manufacture the parts. Since barrel molds are usually of a multi-cavity configuration with many molds containing over 100 cavities, unwinding thread cores adds another degree of complexity of the tool design which increases the mold costs, cycle time and tool maintenance requirements.

Figure 22:
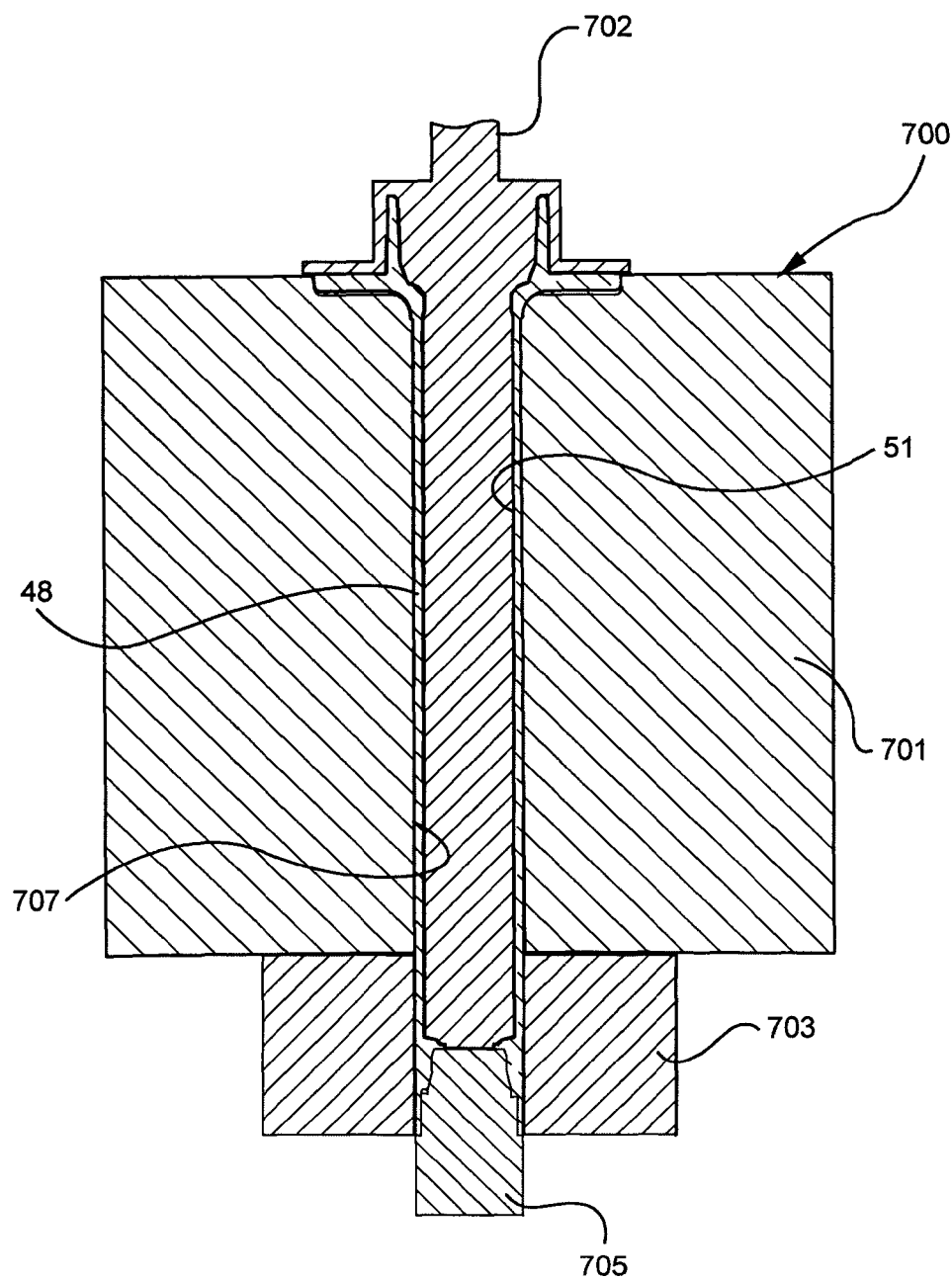
FIG. 22 is a cross-sectional view of an injection mold used to practice the method of the present invention.
Figure 23:
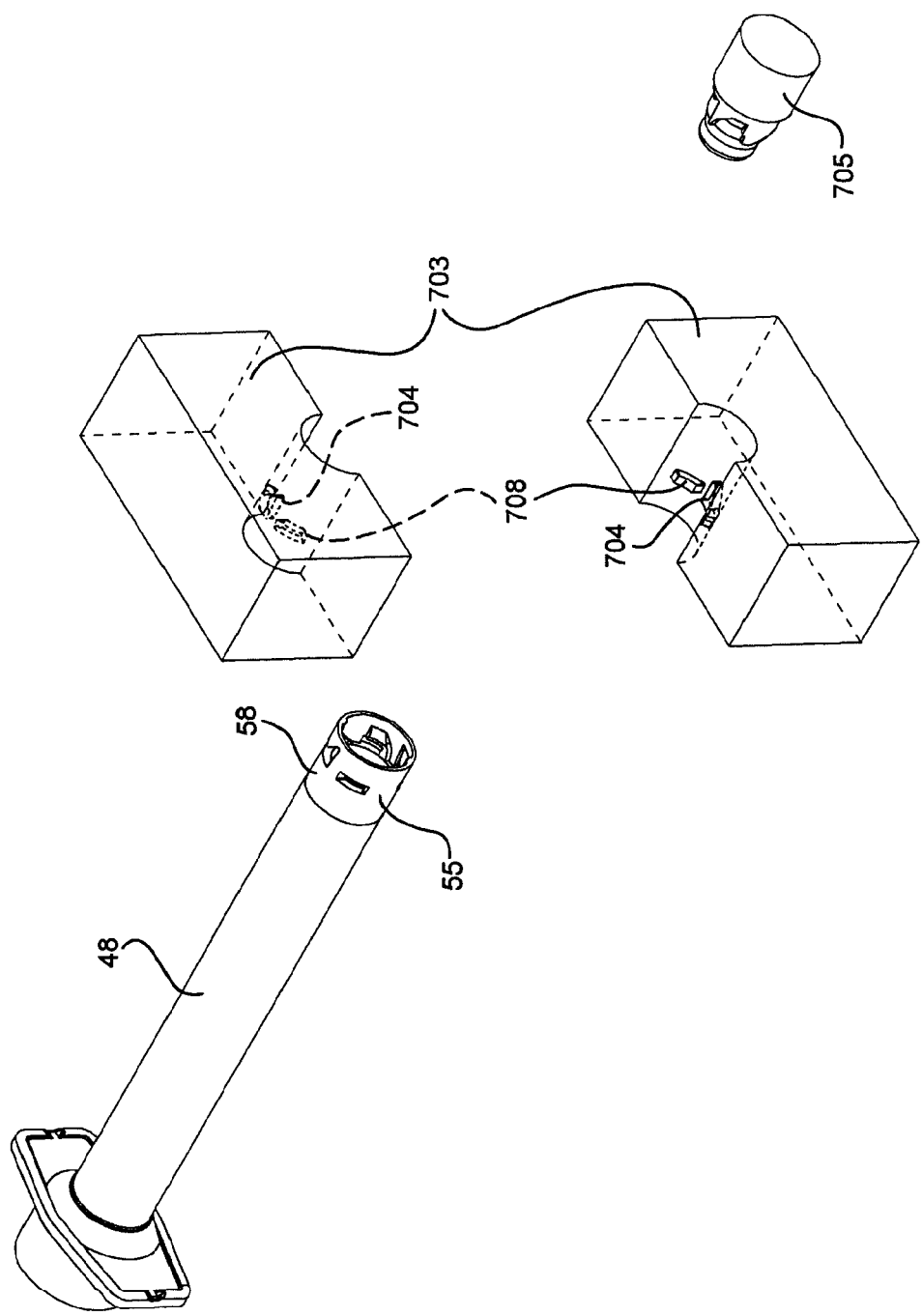
FIG. 23 is an exploded view illustrating the distal end of the syringe barrel along with the stationery straight pull core pin and split core of the injection mold of FIG. 22.

An important aspect of the present invention is a method of making syringe barrels without using an unwinding threaded core. In accordance with the provisions of the present invention, FIGS. 22 and 23 illustrate a process for molding a syringe barrel, such as syringe barrel 48 of FIGS. 4, 5 and 7, described in detail hereinabove. In this embodiment, an injection mold 700 comprises a fixed body portion 701 defining outside surface of barrel 48, a proximal core pin 702 defining chamber 51 in the barrel and movable split cavity 703 defining an outside surface 58 of collar 55. The movable split cavity also include a raised projection 704 for forming an aperture in collar 55 and portions of ramp 59 and rest surface 60. A distal core pin 705 contacts the raised projection on the split cavity 703 when the mold is closed and defines the remaining portions of the interior of the collar. Thus, the fixed portion, the proximal core pin, the movable split cavity and the distal core pin define a cavity 707 in the shape of the syringe barrel.

The method of the present invention further includes injecting molten thermoplastic material into cavity 707 of the mold; allowing enough time for thermoplastic material to solidify enough to allow movement of the barrel with respect to the mold cavity; opening the split cavity so that the raised projection on the split cavity is outside of the collar and removing the proximal core pin and the molded barrel axially from the fixed portion of the mold without rotating the distal core pin, It should be noted that the movable split cavity may also include a second projection 708. The distal core pin is configured to cooperate with the second projection to form a second aperture in the collar and an additional rest surface 366 spaced between ramps 359 and rest surfaces 360 as illustrated on the syringe of FIG. 14.

Also, the raised projection on the split cavity can be further configured to cooperate with the distal core pin to form a guide surface 86 in the collar, running along and spaced from the ramp, for guiding the lug during removal of the needle assembly from the barrel.

A wide variety of thermoplastic materials are suitable for the formation of the syringe barrel using the method of the present invention. Preferably the thermoplastic material is selected from the group consisting of polypropylene, polyethylene, polycarbonate, PET and combinations thereof.

The method of making a syringe barrel of the present invention allows thread-like structures (ramps) to be created without using a threaded core and without producing undercuts. This is achieved by a moving split cavity and a stationery straight pull distal core pin. The distal core pin creates the minor diameter of the ramps, while the major diameter is created by the movable split cavity. This method of creating the ramps results in the simpler tool design that can be done with fewer components than with unwinding methods. Fewer moving parts will require less maintenance. In addition, the action required to open the split cavity is done concurrently with the mold opening movement.

What is claimed is:

1. A method of making an elongate syringe barrel for use with a needle assembly having a hub, said hub including a body portion having an outwardly projecting lug and a proximally facing annular surface, said barrel having a longitudinal axis, an outside surface and an inside surface defining a chamber for retaining fluid, an open proximal end, and open distal end including a collar and a distally facing annular surface projecting into said open proximal end, a portion of said collar including a cylindrically shaped sidewall having an inside surface and an outside surface, a ramp and a rest surface projecting inwardly from said inside surface, said ramp oriented at an acute angle with respect to said longitudinal axis for guiding said lug, during needle assembly attachment, to said rest surface forcing said annular surface on said hub to contact said annular surface in said open proximal end of said barrel, to form a seal between said hub and said barrel, said rotation of said hub with respect to said barrel being less than 180° while said lug travels along said ramp during installation of said needle assembly to said barrel, said method comprising the steps of:

providing an injection mold having a cavity defining a syringe barrel, said mold including a fixed portion defining said outside surface of said barrel, a proximal core pin defining said chamber, a movable split cavity defining said outside surface of said collar and including a raised projection for forming an aperture in said collar and portions of said ramp and said rest surface, and a distal core pin which contacts said raised projection on said movable split cavity when said mold is closed to define remaining portions of said inside surface of said collar;

injecting molten thermoplastic material into said cavity of said mold;

allowing said thermoplastic material to solidify enough to allow movement of said barrel with respect to said mold cavity;

opening said split cavity so that said raised projection is outside of said collar;

removing said proximal core pin and said barrel axially from said fixed portion of said mold without rotation of said distal core pin.

2. The method of claim 1 wherein said thermoplastic material is selected from the group consisting of polypropylene, polyethylene, polycarbonate, PET and combinations thereof.

3. The method of claim 1 wherein said raised projection on said split cavity is configured to cooperate with said distal core pin to form a guide surface running along and spaced from said ramp for guiding said lug during removal of said needle assembly from said barrel.

4. The method of claim 1 wherein said split cavity includes a second projection, and said core pin is configured to cooperate with said second projection to form a second aperture in said collar and a second rest surface.

* * * * *